(12) United States Patent
Gandhi et al.

(10) Patent No.: US 7,968,499 B2
(45) Date of Patent: Jun. 28, 2011

(54) RHAMNOLIPID COMPOSITIONS AND RELATED METHODS OF USE

(75) Inventors: Niranjan R. Gandhi, River Hills, WI (US); Victoria L. Palmer Skebba, Cedarburg, WI (US)

(73) Assignee: Jeneil Biotech, Inc., Saukville, WI (US)

( * ) Notice: Subject to any disclaimer, the term of this patent is extended or adjusted under 35 U.S.C. 154(b) by 183 days.

(21) Appl. No.: 11/705,194

(22) Filed: Feb. 12, 2007

(65) Prior Publication Data

US 2007/0207930 A1    Sep. 6, 2007

Related U.S. Application Data

(60) Provisional application No. 60/772,326, filed on Feb. 10, 2006.

(51) Int. Cl.
*A01N 65/00* (2009.01)
*A01N 25/00* (2006.01)
*A01N 43/04* (2006.01)

(52) U.S. Cl. ............... 504/358; 514/9; 514/54; 424/761

(58) Field of Classification Search ............... 504/358; 514/9, 54; 424/761
See application file for complete search history.

(56) References Cited

U.S. PATENT DOCUMENTS

| | | | |
|---|---|---|---|
| 5,635,443 A | 6/1997 | Lesenko | |
| 5,698,001 A | 12/1997 | Keenportz | |
| 5,767,090 A | 6/1998 | Stanghellini et al. | |
| 6,984,609 B2 | 1/2006 | Devisetty et al. | |
| 2005/0266036 A1* | 12/2005 | Awada et al. | 424/405 |
| 2005/0271780 A1 | 12/2005 | Schroeder et al. | |
| 2006/0233935 A1* | 10/2006 | Van Haesendonck et al. | 426/601 |

FOREIGN PATENT DOCUMENTS

EP    282942    * 9/1988

OTHER PUBLICATIONS

Junco et al., Environ. Sci. Technol. 37, 2988-2996 (2003).*

* cited by examiner

*Primary Examiner* — Chih-Min Kam
(74) *Attorney, Agent, or Firm* — Reinhart Boerner Van Deuren s.c.

(57) ABSTRACT

Compositions comprising a rhamnolipid component and one or more active agents, and related methods of use.

8 Claims, 3 Drawing Sheets

$R_1$ = H, OH, alpha-L-rhamnopyranosyl;

$R_2$ = H, $-\underset{R_4}{CH}-CH_2-COOH$;

$R_3$=($C_5$-$C_{20}$)-saturated, -mono- or poly-unsaturated alkyl;

$R_4$=($C_5$-$C_{20}$)-saturated, -mono- or poly-unsaturated alkyl.

Figure 2

R1 -- α-L-RHAMNOPYRANOSYL-β-HYDROXYDECANOYL
-β-HYDROXYDECANOATE

R2 -- 2-O-α-L-RHAMNOPYRANOSYL-α-L-RHAMNOPYRANOSYL
-β-HYDROXYDECANOYL-β-HYDROXYDECANOATE

Figure 3

RHAMNOLIPID COMPOSITIONS AND RELATED METHODS OF USE

This application claims priority benefit from application Ser. No. 60/772,326 filed 10 FEB, 2006, the entirety of which is incorporated herein by reference.

BACKGROUND OF THE INVENTION

Many biocidic and therapeutic agents, no matter how diverse—in terms of composition or function, have limited utility for one or more of a number of factors ranging from cost to toxicity. Some agents may have toxicity concerns precluding efficacious use. Others, while perhaps safe at useful concentrations, may be cost prohibitive.

For instance, the natural antibacterial agent nisin is commonly used as a preservative in many heat-processed and low-pH foods. A fermentation product of *Lactococcus lactis* (formerly known as *Streptococcus lactis*), it is commercially produced from cultured milk or by the fermentation of other substrates. Several factors, including one or more complex polycyclic structures, preclude synthesis. Highly controlled fermentation and isolation techniques contribute to its high cost and limited utility.

On the other hand, an antimycotic agent such as natamycin, while costly, presents other issues. Toxicity and related regulatory concerns have limited application to ophthalmic suspensions (i.e., eye drops) and treatment of selective cheese products, meats, sausages, seafood and the like to prevent or reduce mold spoilage. As a fermentation product of *Streptomyces natalensis* and other species, it also has a complex chemical structure precluding economical, large scale synthesis.

The search for effective, economical delivery of an active agent has been an ongoing concern in the art. Likewise, the formulation of various compositions, whether or not biocidic or therapeutic, has been a subject of continued research. Various carriers, emulsifiers, and the like can aid delivery of a composition, but often do not promote performance. As a result, efforts continue toward the development of components and formulations which can enhance the benefits available from such compositions.

SUMMARY OF THE INVENTION

In light of the foregoing, it is an object of the present invention to provide one or more surface active and/or emulsifier components useful in conjunction with various compositions or formulations of active agents, thereby overcoming deficiencies and shortcomings in the art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to provide various compositions or formulations comprising one or more active agents or components exhibiting enhanced effect at reduced levels, as compared to compositions of the prior art.

It can be another object of this invention to provide compositions comprising a component to enhance delivery of an active agent, thereby promoting beneficial performance, regardless of whether such a component can be construed as a surfactant or an emulsifier.

It can also be an object of the present invention to provide a method of using such a component to enhance delivery and/or effect of an active agent/component or composition thereof.

Other objects, features, benefits and advantages of the present invention will be apparent from this summary and descriptions of certain embodiments and will be readily apparent to those skilled in the art having knowledge of various active agents, compositions thereof and their formulation techniques. Such objects, features, benefits and advantages will be apparent from the above as taken into conjunction with the accompanying examples, data, figures and all reasonable inferences to be drawn therefrom, alone or with consideration of the references incorporated herein.

In part, the present invention can comprise a composition comprising an active agent/biocide component selected from nisin, natamycin and combinations thereof, and a rhamnolipid and/or a carrier component comprising a rhamnolipid. In certain embodiments, a rhamnolipid can be selected from a monorhamnolipid, a dirhamnolipid and combinations thereof. Such a rhamnolipid can be present in an amount sufficient to reduce the effective concentration of the active agent to less than that otherwise effective in the absence of such a rhamnolipid.

Figure 1A:
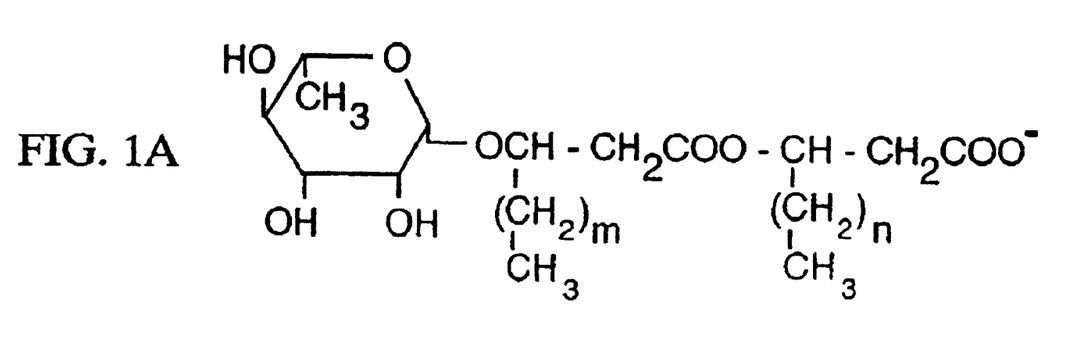
FIGS. 1A-B and 2 illustrate structures of several non-limiting, representative monorhamnolipid and dirhamnolipid compounds.
Figure 1B:
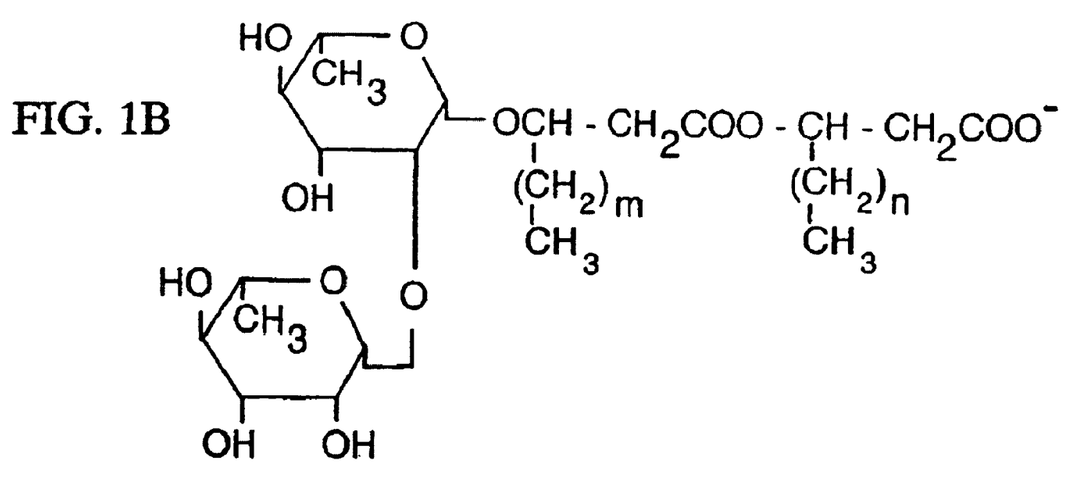
Figure 2:
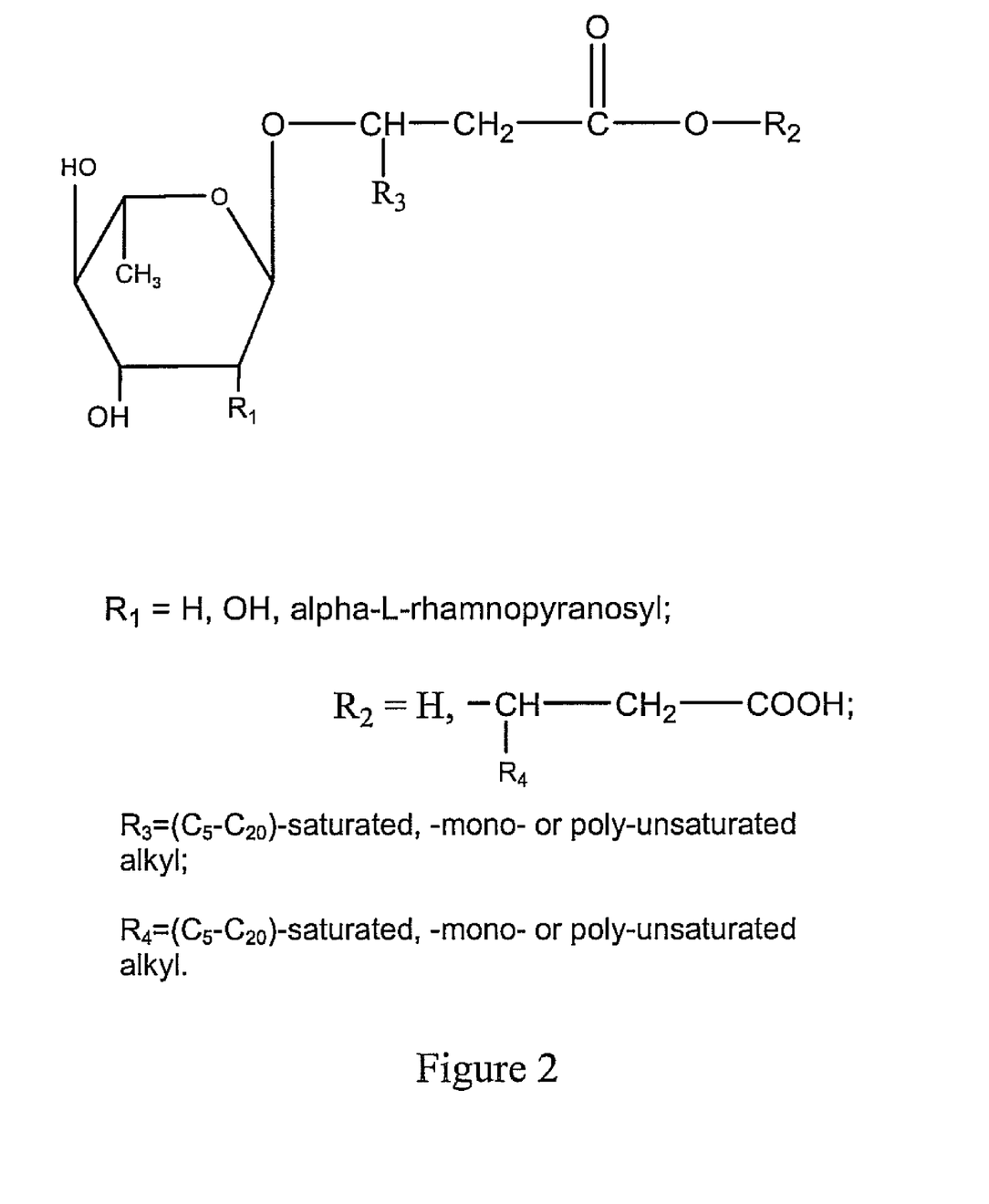

In accordance with this invention, as would be understood by those skilled in the art, a rhamnolipid can comprise one or more compounds of the sort described in U.S. Pat. Nos. 5,455,232 and 5,767,090, each of which is incorporated herein by reference in its entirety. Such a rhamnolipid compound, whether presently known in the art or hereafter isolated and/or characterized, can be of a structure disclosed therein or varied, as would also be understood by those skilled in the art. For example, without limitation, whether synthetically-derived or naturally-occurring (e.g., from a *Pseudomonas* species or a strain thereof) in an acid form and/or as a corresponding acid salt, such a compound can be alkyl- and/or acyl-substituted (e.g., methyl and/or acetyl, respectively, and higher homologs thereof) at one or more of the saccharide hydroxy positions, or otherwise derivatized as would be known in the art. Likewise, whether in mono- and/or dirhamno form, any such compound can be varied by hydrophobic moiety. As non-limiting examples, with reference to FIGS. 1A-B and 2, m and n can independently range from about 4 to about 20, regardless of whether such hydrocarbon moieties are saturated, monounsaturated or polyunsaturated, whether the hydrophobic moiety is protonated, present as the conjugated base with any available counterion or otherwise derivatized. Consistent with broader aspects of this invention, a rhamnolipid useful in such compositions is structurally limited only by resulting surface active function and/or emulsifier effect in conjunction with a nisin and/or a natamycin agent. Accordingly, structural variations of the sort described in International Publication WO 99/43334 are also considered in the context of this invention, such publication incorporated herein by reference in its entirety.

A nisin antibacterial component can comprise one or more compounds of a mixture of polypeptide compounds presently known in the art or hereafter isolated or characterized, including but not limited to one or more compounds demonstrating antibacterial properties, as described in U.S. Pat. Nos. 2,935,503, 5,755,614, 5,527,505 and 6,110,509, each of which is incorporated herein by reference in its entirety. While generally understood in the context of certain number(s) and/or order(s) of amino acid or modified amino acid residues, such compounds can vary by length and/or residue identity or sequence, limited only by natural, recombinant and/or mutant expression (e.g., by *Lactococcus lactis* or strains thereof) or available synthetic technique. For instance, while such compounds can be characterized as having amino acid residues or cyclic moieties thereof, various other peptide structures are contemplated, regardless of residue identity, number or sequence between the N- and C-terminals. Likewise, whether naturally-occurring or synthetically-derived consistent with a broader aspect of this invention, such nisin components are limited only by inhibitive effect on Gram-positive bacteria and/or spore-forming bacteria, alone or in conjunction with a rhamnolipid of the sort described above.

A natamycin antimycotic component can comprise one or more compounds presently known in the art or hereafter isolated or characterized, such compounds including but not limited to one or more compounds demonstrating antimycotic properties described in U.S. Pat. Nos. 6,844,004, 6,146,675 and 6,369,036, each of which is incorporated herein by reference in its entirety. While generally understood in the context of a certain polycyclic structure and molecular weight, such compounds can vary, limited only by natural, recombinant and/or mutant expression (e.g., by *Streptomyces natalensis* and related species and strains thereof) or available synthetic technique. For instance, while certain such compounds can be characterized as having free acid and amine functionalities, various salts and other derivatives are contemplated. Likewise, whether naturally-occurring or synthetically-derived, such compound can vary by stereochemistry, as well as the position and/or degree of hydroxy substitution thereon. Consistent with a broader aspect of this invention, such natamycin components are limited only by antimycotic effect, alone or in conjunction with a rhamnolipid of the sort described above.

In part, this invention can also be directed to compositions comprising an active agent selected from one or more plant nutrients, such nutrients including but not limited to magnesium, potassium, iron, copper, manganese, zinc, boron, molybdenum, cobalt, and nickel, together with compounds, salts, hydrates, solvates and/or complexes thereof—any in combination one with the other. Without limitation, such agents, regardless of amount or concentration (e.g., whether or not construed a micronutrient) can include those described in U.S. Pat. No. 5,962,717 the entirety of which is incorporated herein by reference. In certain embodiments, such a composition can comprise a mono-rhamnolipid, a dirhamnolipid and combinations thereof.

In part, this invention can also be directed to compositions comprising an active agent selected from one or more human or animal dietary nutrients, such nutrients including but not limited to vitamins, minerals, together with compounds, salts, hydrates, derivatives, solvates and/or complexes thereof—any in combination one with the other. Without limitation, such agents, regardless of amount or concentration (e.g., whether or not construed a micronutrient) can include those described in the aforementioned '717 patent and U.S. Pat. No. 6,503,545, the entirety of which is incorporated herein by reference. While various compositions or formulations in the '545 patent are described as milk or protein-based, in combination with one or more nutrients, various other compositions comprising other such vitamins, minerals and nutrients can be incorporated into a dietary supplement comprising a mixture, emulsion and/or suspension of such components. In certain embodiments, such a composition or formulation can comprise a monorhamnolipid, a dirhamnolipid and combinations thereof.

In part, this invention can also be directed to compositions comprising an active agent selected from one or more insecticides, whether synthetic or naturally-occurring, together with salts, hydrates, derivatives, solvates and/or complexes thereof—any in combination one with the other. Regarding the former, such insecticides can comprise any one or more of a range of organophosphorous compounds, including but not limited to those available under the diazinon and malathion trade designations. Without limitation, such insecticidal agents can include those described in U.S. Pat. No. 6,566,349, the entirety of which is incorporated herein by reference. Regarding the latter, such naturally-occurring insecticidal agents include but are not limited to those comprising azadirachtin and structurally-related compounds extractable from various parts of the neem tree. Without limitation, such agents can include those described in U.S. Pat. No. 6,811,790, the entirety of which is incorporated herein by reference. Regardless of identity of the insecticidal active agent, in certain embodiments, such a composition can comprise a monorhamnolipid, a dirhamnolipid and combinations thereof.

In part, this invention can also be directed to compositions comprising an active agent selected from one or more herbicides, such herbicides including but not limited to N-phosphonomethylglycine, available under the Round-Up trade designation and various other agents available under the alachlor, asulam and imazethapyr trade designations, and 2,4-dichlorophenoxyacetic acid (i.e., 2,4-D), together with salts, hydrates, derivatives, solvates and/or complexes thereof—any in combination one with the other. Without limitation, such agents, regardless of amount or concentration can include those described in U.S. Pat. Nos. 6,184,182 and 6,232,272, each of which is incorporated herein by reference. In certain embodiments, such a composition can comprise a monorhamnolipid, a dirhamnolipid and combinations thereof.

In part, this invention can also be directed to compositions comprising an active agent selected from one or more plant hormone and/or growth regulators, such hormones/regulators including but not limited to indole 3-acetic acid, gibberellin, humic acids, and various other known plant auxins, together with salts, hydrates, derivatives, solvates and/or complexes thereof—any in combination one with the other. Without limitation, such agents, regardless of amount or concentration can include those described in U.S. Pat. Nos. 5,635,443, 6,984,609 and 5,698,001, each of which is incorporated herein by reference in its entirety. In certain embodiments, such a composition can comprise a monorhamnolipid, a dirhamnolipid and combinations thereof.

In part, this invention can also be directed to compositions comprising an active agent selected from amylose, amylopectin and combinations thereof. Such compositions can be considered in the context of bread or bakery products, regardless of origin of the component flour, starch (e.g., wheat, corn, soy, rice, etc.) or active agents thereof. Without limitation, amylose and amylopectin are described in the context of bakery compositions in U.S. Pat. Nos. 4,416,903 and 6,635,289, each of which is incorporated herein by reference in its entirety. In certain embodiments, such a composition can comprise a rhamnolipid selected from a monorhamnolipid, a dirhamnolipid and combinations thereof. In this compositional context, such a rhamnolipid can be present in an amount at least partially sufficient to inhibit amylose and/or amylopectin retrogradation and/or bakery staling. Alternatively, such a rhamnolipid component can be present in an amount at least partially sufficient to provide a humectant function, retain moisture and/or maintain bakery texture.

Without regard to active agent or rhamnolipid identity, the inventive compositions can comprise a carrier component and/or a fluid component selected from, but not limited to, water, an alcohol or another organic solvent, an oil, a gas and combinations thereof. For instance, while such compositions are unlimited with respect to amount of antibacterial, antimycotic or rhamnolipid quantities, a carrier comprising water and/or an alcohol can be used to facilitate desired formulation, shipping, storage and/or application properties, as well as effective concentration and resulting activity. Accordingly, various embodiments can also comprise a gaseous carrier component, such compositions as can be administered with a suitable propellant or as an aerosol.

In certain embodiments of this invention, such a composition can be on, or as can be applied to, a substrate or surface susceptible to, supporting or supportive of bacterial or mycotic (e.g., yeast and/or fungi) growth. Accordingly, such a substrate or surface can comprise any material which can, is capable of or does support bacterial or mycotic growth. Such substrates can comprise inanimate materials such as but not limited to wood, ceramics, porcelain, stone, metal, plaster, drywall, cement, fabrics, leather, plastics and the like. Accordingly, such substrates can be selected from the available range of building materials/surfaces, consumer products and/or articles of manufacture.

In various other embodiments, substrates can be selected from any perishable human or animal food material including but not limited to raw and processed fruits, vegetables, cereals (e.g., wheat, corn, rice, oats, soy, etc.), meats (beef, pork, lamb, poultry, fish, seafood, etc.), eggs, dairy products, cultured dairy products, fruit and vegetable juices and related drink products, fermented beverages (e.g., wine and beer) and related food stuff (e.g., sauces, gravies, mayonnaise, cured or processed meats and meat products, canned goods and the like). Generally, substrates contemplated in the context of this invention include any material or surface susceptible to either Gram-positive bacteria or mycotic growth, in the context of nisin and natamycin compositions, respectively.

In certain other embodiments, such a composition can be on, or as can be applied to, a substrate comprising a cellulosic component which can, is capable of or does support mycotic growth. Without limitation, certain embodiments can comprise plants, plant components (e.g., roots, stems, leaves, produce and the like) and any originating shoots or seeds. In particular, without limitation, such compositions can be on any plant produce, whether termed a fruit, vegetable, tuber, flower, seed or nut, whether before or post-harvest. Certain such plants and/or produce therefrom are recognized in the art, alone or collectively, as agricultural crops. Accordingly, in certain embodiments, a composition of this invention can be on or applied to such a crop at any time during development, pre-harvest and/or post-harvest.

In certain other embodiments, various compositions of this invention can be on, in contact with, or as applied or administered to a substrate or surface comprising mammalian or human tissue, including but not limited to nails, hair, skin and other cellular material, in the context of a pharmaceutical formulation for the treatment or prevention of bacterial or mycotic growth or infection. Representative compositions are described, below, in terms at least in part applicable to one or more other embodiments.

In part, the present invention can also be directed to a composition for inhibiting or preventing bacterial or mycotic growth, such a composition comprising a biocide component, respectively, an antibacterial (e.g., a nisin) or antimycotic (e.g., a natamycin) component of the sort described herein and a rhamnolipid surfactant component of the sort also described herein. Whereas each component, separately and individually, can have a certain biocidic activity, a composition thereof can provide an enhanced activity greater than any one component activity or the sum thereof. As demonstrated below, the rhamnolipid surfactant component can be in an amount at least partially sufficient to reduce the effective amount of the antibacterial or antimycotic component to less than that otherwise effective, in the absence of a rhamnolipid component, to maintain substantially the same or comparable level of activity. Refer to co-pending application Ser. No. 11/351,572, filed Feb. 10, 2006, the entirety of which is incorporated herein by reference, and the rhamnolipids and use described therein, such rhamnolipids and use as can be extended to the present methods and compositions, such use and effect as would be understood by those skilled in the art made aware of this invention. Regardless of rhamnolipid identity or amount thereof, such compositions can comprise a nisin component, a natamycin component and combinations thereof. Likewise, such compositions can further comprise one or more other components or active agents to provide the composition multiple activities. For instance, such compositions can include but are not limited to herbicidal and pesticidal components, as well as those others providing a range of biocidic activity.

Accordingly, as demonstrated below, the present invention can also comprise a method of using a rhamnolipid to improve biocidic, antibacterial and/or antimycotic effect. Such a method can comprise providing an active component selected from a nisin, a natamycin and combinations thereof, such a component having a first bio-inhibitory concentration for inhibition of bacterial or mycotic growth; and contacting the component and a rhamnolipid surfactant component, with the rhamnolipid component in an amount at least partially sufficient to improve effect and the active component at a second bio-inhibitory concentration less than the first inhibitory concentration. As such, an improvement can be quantitatively and/or qualitatively demonstrated by a zone of inhibition maintained or substantially unchanged at a lower concentration of active component. Various embodiments of such a methodology can comprise reducing the rhamnolipid component concentration, as desired, without substantial loss of biocidic or inhibitory effect.

In the alternative, the present invention can be directed to a system comprising one or more of the present compositions on or in contact with a substrate comprising at least one of a yeast membrane, bacterial membrane and a mycotic membrane. Such a composition can comprise a carrier component comprising a rhamnolipid in an amount at least partially sufficient to reduce the effective concentration of an active component with respect to the membrane. In certain embodiments, the rhamnolipid component can be used advantageously in an amount sufficient to reduce any mammalian toxicity associated with an active/biocide component. In some such and certain other embodiments, the effective concentration of the biocide component can be reduced up to and/or greater than about 50%. Regardless of rhamnolipid identity, the bacterial and/or mycotic membranes of such a system can be on or in contact with a substrate of the sort including but not limited to those mentioned above.

Regardless of the presence of mycotic or bacterial organisms at any point in time, the present invention can also provide a method of inhibiting growth. Such a method can comprise providing a composition of the sort described herein, and contacting a substrate therewith. In certain embodiments, as can comprise a natamycin component, such a substrate can comprise a cellulosic component, such as but not limited to a plant or a seed. Contact can be through a growth medium such as soil or a hydroponic environment, an irrigation medium, and/or by way of a substrate surface coating, such as a film or residue on a seed. Alternatively, such a composition can be applied directly to a plant or its produce, whether pre- or post-harvest, to inhibit current and/or prospective growth.

In certain other embodiments, as can comprise a nisin and/or natamycin component, such a substrate can comprise a perishable food material of the sort described above, packaging for such materials and food handling and/or processing equipment. In certain other embodiments, as can comprise a nisin component, such a substrate can comprise mammalian or human tissue, medical or clinical instruments or articles of manufacture and/or material surfaces associated with the known range of health care facilities and environments.

DETAILED DESCRIPTION OF CERTAIN EMBODIMENTS

Without limitation to any particular theory or mode of operation, the increased activity and/or effect exhibited by compositions of this invention may be due at least in part to the surface active nature of the rhamnolipid component. In particular, a rhamnolipid biosurfactant may open and/or enhance pore formation in the plasma membrane of the host organism, increasing cell permeability and therefore susceptibility of the cell to the active component. It is believed that an antibacterial or antimycotic agent can reach its target and alter cell membrane function much more effectively in the presence of a rhamnolipid. As such, effective formulations can be achieved using lower concentration levels of either an active agent or a rhamnolipid component.

As mentioned above, the present invention can be directed to a method for using a rhamnolipid to reduce the effective amount of an active component required to achieve a given level of inhibition or activity. In certain embodiments, as illustrated in several of the following examples, the concentration of an active component can be reduced to or below a regulatory and/or governmentally acceptable and/or approved level of use. Reducing the effective amount of active agent or biosurfactant component required for a given level of antibacterial or antimycotic activity can provide a range of compositional formulations that leave less residue on a food product—resulting in lower production and application costs while meeting or exceeding regulatory environmental and toxicity standards.

The relative amounts or concentrations of active component and biosurfactant component in the compositions of the present invention can vary widely within effective ranges. The concentrations and/or doses utilized are preferably selected to achieve an enhanced or increased activity over the individual components alone and/or to maximize the activity of the composition at the lowest effective component concentration(s). Accordingly, the weight ratios and/or concentrations yielding such enhanced activity depend not only on the specific active agent and rhamnolipid component utilized, but on the specific end-use application of the composition including, but not limited to, climate, soil composition, nature of the host and/or potential exposure to a particular bacterial or mycotic growth.

The compositions of the present invention can be used as dispersions or emulsions and are available in the form of a concentrate containing a high proportion of the antibacterial/antimycotic-biosurfactant system, as can be diluted (e.g., water or another fluid component) before use. These concentrates should preferably be able to withstand storage for prolonged periods and after such storage, where applicable be capable of dilution (e.g., with water) in order to form (e.g., aqueous) preparations which remain homogeneous for a sufficient time to enable them to be applied by conventional methods and equipment.

Depending on end-use application, the compositions of the present invention may also comprise any other required components including, but not limited to, solid or liquid carriers to facilitate application, surfactants, preservatives, protective colloids, adhesives, thickeners, thixotropic agents, penetrating agents, stabilizers, sequestrants, texturing agents, flavoring agents (for post-harvest applications), sugars, colorants, etc., as will be well known to those skilled in the art.

For example, the compositions can be applied to foodstuffs or used for agricultural purposes and formulated with such a carrier or diluent. With regard to the latter, the compositions can be applied, formulated or unformulated, directly to the foliage of a plant, to seeds or to other medium in which plants are growing or are to be planted, or they can be sprayed on, dusted on or applied as a cream or paste formulation, or they can be applied as a vapor or as slow release granules. Application can be to any part of the plant including the foliage, stems, branches or roots, or to soil surrounding the roots, or to the seed before it is planted, or to the soil generally, to irrigation water or to hydroponic culture systems. The inventive compositions can also be injected into plants or sprayed onto vegetation using electrodynamic spraying techniques or other low volume methods.

In certain embodiments, the compositions may be in the form of dustable powders or granules comprising a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent. The compositions may also be in the form of wettable powders or water dispersible granules comprising wetting or dispersing agents to facilitate the dispersion in liquids. The powders and granules may also contain fillers and suspending agents. Alternatively, the compositions may be used in a micro-encapsulated form. They may also be formulated in biodegradable polymeric formulations to obtain a slow, controlled release of the active substance.

Regardless, such solid formulations can comprise a range of forms and shapes, including but not limited to cylinders, rods, blocks, capsules, tablets, pills, pellets, strips, spikes and the like. Alternatively, granulated or powdered material can be pressed into tablets or used to fill a range of capsules or shells. Regardless, such formulations can be used to introduce the present compositions into a soil or related growth medium, in the vicinity of or proximate to the roots of a plant.

In such embodiments, whether compositionally comprising a powder, dust, or granule, such compositions can be inserted into the soil in the form of spikes, rods, or other shaped moldings.

Emulsifiable concentrates or emulsions may be prepared by dissolving the active ingredients of the present invention in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers. Compositions to be used as sprays may be in the form of aerosols wherein the formulation is held in a container under pressure of a propellant, e.g., fluorotrichloromethane or dichlorodifluoromethane.

Whether or not emulsified or dispersed or dissolved in a fluid component, such rhamnolipid/active agent mixtures can be further combined with one or more of a range of solid or particulate carrier components, examples of which are provided elsewhere herein. Such carrier components can be of the sort described above for use in conjunction with plant or agricultural applications. Conversely, various food-grade carrier components are known in the art. Such carrier components include but are not limited to a range of food-grade carbohydrate and protein-based materials. An active agent, such as nisin or natamycin, can be introduced or contacted with such a carrier before or after combination with a rhamnolipid component.

As mentioned above, certain compositions and methods of this invention can find utility in the pharmaceutical context. Accordingly, the antibacterial, antimycotic and rhamnolipid components of this invention contain one or more acidic or basic functional groups and are, thus, capable of forming salts and pharmaceutically-acceptable salts with pharmaceutically-acceptable acids and bases. The term "pharmaceutically-acceptable salts" refers to the relatively non-toxic, inorganic and organic acid and base addition salts of such compounds. Such salts can be prepared by reacting the component compound with a suitable acid or base. Suitable bases include the hydroxide, carbonate or bicarbonate of a pharmaceutically-acceptable metal cation, ammonia, or a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. Representative acid addition salts include the hydrobromide, hydrochloride, sulfate, phosphate, nitrate, acetate, valerate, oleate, palmitate, stearate, laurate, benzoate, lactate, phosphate, tosylate, citrate, maleate, fumarate, succinate, tartrate, napthalate, mesylate, glucoheptonate, lactobionate, and laurylsulphonate salts and the like.

As mentioned above, the components, compositions and the pharmaceutically-acceptable salts of this invention, are antibacterial or antimycotic inhibitors. Tests, methods and assays for bacterial and mycotic inhibition are well known in the art. Thus, yeast, fungi or bacteria can be inhibited by contacting the growth with an effective amount of an inventive composition or by contacting a substrate/surface supportive of such growth with an effective amount of such a composition. The contacting may take place in vitro or in vivo.

"Contacting" means that an antimycotic composition and the substrate/surface are brought together so that the composition can interact with growth thereon or later developed. Amounts of a composition effective to inhibit growth may be determined empirically, and making such determinations is within the skill in the art. Inhibition includes both reduction and elimination of mycotic or bacterial growth.

To treat an animal or human subject having a mycotic or bacterial growth or suffering from infection, an effective amount of one or more of the present compositions, optionally including one or more pharmaceutically-acceptable component salts, can be administered as would be understood in the art. Effective dosage forms, modes of administration and dosage amounts may be determined empirically, and making such determinations is within the skill of the art. It is understood by those skilled in the art that the dosage amount will vary with the activity of the particular compound employed, the severity of the infection, the route of administration, the rate of excretion of the compound, the duration of the treatment, the identity of any other drugs being administered to the animal/subject, the age, size and species of the animal/subject, and like factors well known in the medical and veterinary arts. In general, a suitable daily dose will be that amount which is the lowest dose effective to produce a therapeutic effect. The total daily dosage will be determined by an attending physician or veterinarian within the scope of sound medical judgment. If desired, the effective daily dose of such a composition may be administered as two, three, four, five, six or more sub-doses, administered separately at appropriate intervals throughout the day. Animals treatable according to the invention include mammals. Mammals treatable according to the invention include dogs, cats, other domestic animals, and humans.

Compositions of this invention may be administered to an animal/patient for therapy by any suitable route of administration, including orally, nasally, rectally, intravaginally, parenterally, intracisternally and topically, as by powders, ointments or drops, including buccally and sublingually. The preferred routes of administration are orally and topically.

While it is possible for the active component(s) of such compositions to be administered individually or sequentially, it is preferable to administer the active ingredient(s) as a pharmaceutical formulation (composition). The compositions of the invention can comprise the active ingredient(s) in admixture with one or more pharmaceutically-acceptable carriers and, optionally, with one or more other compounds, drugs or other materials. Each carrier is "acceptable" in the sense of being compatible with the other ingredients of the formulation and not injurious to the patient.

Regardless of the route of administration selected, the active ingredient(s) is/are formulated into pharmaceutically-acceptable dosage forms by conventional methods known to those skilled in the art. The amount of the active ingredient(s) or component(s) which will be combined with a carrier material to produce a single dosage form will vary depending upon the host being treated, the particular mode of administration and all of the other factors described above. The amount of the active ingredient(s) which will be combined with a carrier material to produce a single dosage form will generally be that amount of the active ingredient(s) which is the lowest dose effective to produce a therapeutic effect.

Methods of preparing pharmaceutical formulations or compositions include the step of bringing the component(s) into association with a carrier and, optionally, one or more accessory ingredients. In general, the formulations are prepared by uniformly and intimately bringing the active ingredient(s) into association with liquid carriers, or finely divided solid carriers, or both, and then, if necessary, shaping the product.

Formulations of the invention suitable for oral administration may be in the form of capsules, cachets, pills, tablets, powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia), and/or as mouthwashes and the like, each containing a predetermined amount of the active ingredient(s). The active ingredient(s) or component(s) may also be administered as a bolus, electuary or paste.

In solid dosage forms of the invention for oral administration (capsules, tablets, pills, dragees, powders, granules and the like), the active ingredient(s) is/are mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethyl-cellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using one or more binders (for example, gelatin or hydroxypropylmethyl cellulose), lubricants, inert diluents, preservatives, disintegrants (for example, sodium starch glycolate or cross-linked sodium carboxymethyl cellulose), surface-active or dispersing agents. Molded tablets may be made by molding in a suitable machine a mixture of the powdered active ingredient(s) moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient(s) therein using, for example, hydroxypropylmethyl cellulose in varying proportions to provide the desired release profile, other polymer matrices, liposomes and/or microspheres. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient(s) can also be in microencapsulated form.

Liquid dosage forms for oral administration of the active ingredient(s) include pharmaceutically-acceptable emulsions, microemulsions, solutions, suspensions, syrups and elixirs. In addition to the active ingredient(s), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents. Suspensions, in addition to the active ingredient(s), may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration of the active ingredient(s) include powders, sprays, ointments, pastes, creams, lotions, gels, solutions, patches and inhalants. The active ingredient(s) may be mixed under sterile conditions with a pharmaceutically-acceptable carrier, and with any buffers, or propellants which may be required.

The ointments, pastes, creams and gels may contain, in addition to the active ingredient(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the active ingredient(s), excipients such as lactose, talc, silicic acid, aluminum hydroxide, calcium silicates and polyamide powder, or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of the active ingredient(s) to the body. Such dosage forms can be made by dissolving, dispersing or otherwise incorporating the active ingredient(s) in a proper medium, such as an elastomeric matrix material. Absorption enhancers can also be used to increase the flux of the active ingredient(s) across the skin. The rate of such flux can be controlled by either providing a rate-controlling membrane or dispersing the active ingredient(s) in a polymer matrix or gel.

Pharmaceutical compositions of this invention suitable for parenteral administration comprise the active ingredient(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monostearate and gelatin.

In some cases, in order to prolong the effect of the active ingredient(s), it is desirable to slow the absorption of the drug from subcutaneous or intramuscular injection. This may be accomplished by the use of a liquid suspension of crystalline or amorphous material having poor water solubility. The rate of absorption of the active ingredient(s) then depends upon its/their rate of dissolution which, in turn, may depend upon crystal size and crystalline form. Alternatively, delayed absorption of parenterally-administered active ingredient(s) is accomplished by dissolving or suspending the active ingredient(s) in an oil vehicle.

Injectable depot forms are made by forming microencapsule matrices of the active ingredient(s) in biodegradable polymers such as polylactide-polyglycolide. Depending on the ratio of the active ingredient(s) to polymer, and the nature of the particular polymer employed, the rate of release of the active ingredient(s) can be controlled. Examples of other biodegradable polymers include poly(orthoesters) and poly (anhydrides). Depot injectable formulations are also prepared by entrapping the active ingredient(s) in liposomes or microemulsions which are compatible with body tissue. The injectable materials can be sterilized for example, by filtration through a bacterial-retaining filter.

The formulations may be presented in unit-dose or multi-dose sealed containers, for example, ampoules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

While part of the preceding discussion is provided in the context of pharmaceutical compositions, it will be understood by those skilled in the art that various aspects thereof are also applicable to compositions and methods directed to the growth, treatment and viability of plants and their produce. Accordingly, as would be understood by those in the art, such compositions—in particular, natamycin compositions—can comprise and/or be applied in the form of pastes, gels, coatings on the surface of a plant or produce. Further, the compositions can comprise and/or be applied as a dust, powder or granule on any such plant or produce. Whether solid or semi-solid, such compositions can comprise and/or be applied using components known in the art to promote wetting or adhesion on such a plant or produce.

Likewise, it will be understood by those skilled in the art that various aspects of the preceding discussion are also applicable to compositions and methods directed to the treatment and/or preservation of perishable food materials. Accordingly, such compositions, whether including a nisin and/or a natamycin component, can comprise and/or be applied with any carrier component comprising a suitable, food grade fluid, suspension or matrix, such compositions comprising and/or applied using compatible components known in the art as may be useful to promote wetting or adhesion on such substrates.

EXAMPLES OF THE INVENTION

The following non-limiting examples and data illustrate various aspects and features relating to the compositions and methods of this invention. Such aspects and features include the surprising and unexpected results obtained using a range of rhamnolipid components, alone or in conjunction with a range of active agents of the sort described herein, including but not limited to antibacterial, antimycotic, nutrient and/or starch components—in the preparation of the inventive compositions. It should, of course, be understood that these examples are included for illustrative purpose only and that the invention is not limited to the particular combinations of materials, conditions, properties or the like set forth herein. Comparable utility and advantages can be realized using various other rhamnolipid components, active agents, methodologies and/or compositional embodiments consistent with the scope of this invention.

All components and/or ingredients used in conjunction with the present invention are commercially available from sources well-known to those skilled in the art. Likewise, the various process parameters described herein can be readily modified by such individuals to account for variations in the identity or concentration of such components and ingredients or as required to achieve results in accordance with those described herein.

Example 1

Nisin is commercially available under the Nisitrol trade designation from Jeneil Biotech, Inc. (Saukville, Wis.) and under the Nisaplin trade designation from Aplin & Barrett Ltd. (Trowbridge, England), containing about 1 million IU per gram. Higher activity preparations (e.g., about 4 million IU per gram, and higher) are commercially-available from other sources known in the art. More generally, nisin can be obtained by isolating the naturally-occurring material from cultures of *Lactococcus lactis*, then concentrating the material according to known methods. See, e.g., U.S. Pat. No. 2,935,503 the entirety of which is incorporated herein by reference. Altered *Lactococcus* strains can also be used to obtain nisin (See, U.S. Pat. No. 4,716,115, also incorporated herein by reference in its entirety.)

Example 2

Natamycin is commercially available under the Natajen trade designation from Jeneil Biotech, Inc. (Saukville, Wis.) and under the Delvocid® trade designation from Gist-Brocades Food Ingredients, Inc. (King of Prussia, Pa.) or under the Natamax designation from Cultor Food Science. Commercially available natamycin can be obtained in pure form, or may be cut or delivered with a carrier such as lactose or sodium chloride.

Example 3

Figure 3:
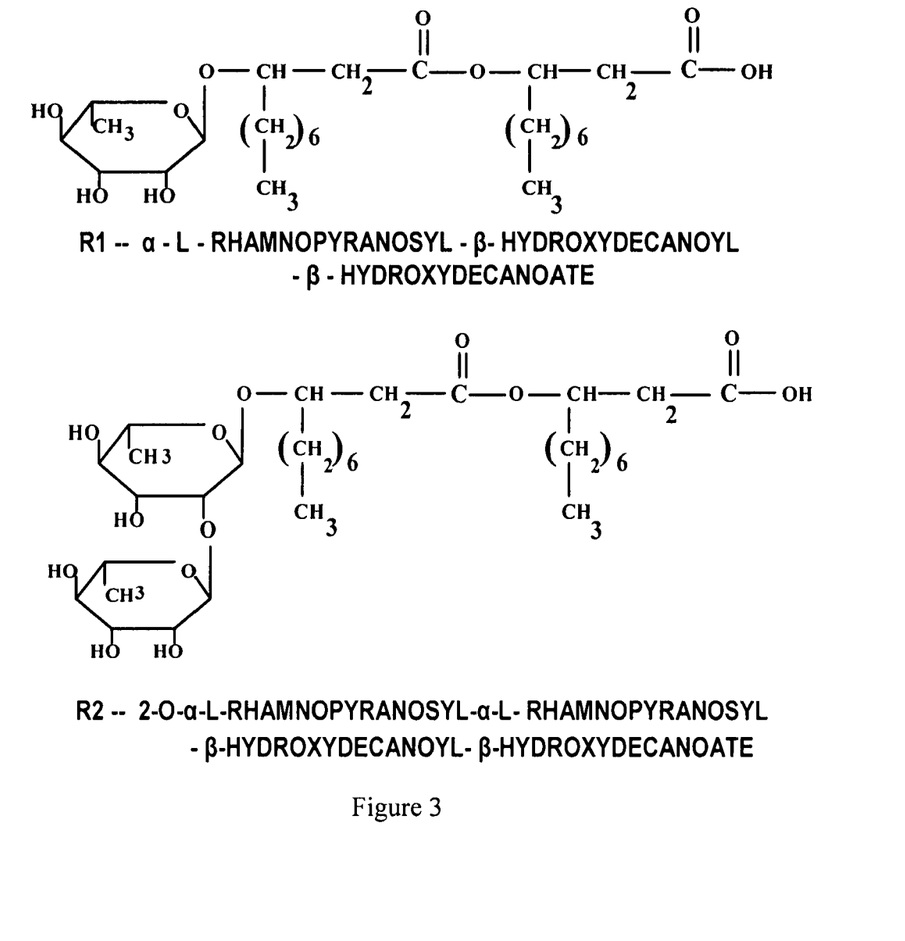
FIG. 3 provides two embodiments of a rhamnolipid component, designated R1 and R2 for the respective mono- and dirhamnolipid structures, which can be used in combination one with the other, as described in several of the followings examples.

As mentioned above, rhamnolipid is commercially available under the Zonix trade designation from Jeneil Biotech, Inc. (Saukville, Wis.) as a combination of mono- and dirhamnolipids, R1 and R2, as shown in FIG. 3, over a range of concentrations. Such products can be modified, as needed. Representative of but one aspect of the compositions of this invention, an aqueous concentrate (e.g., 25 weight %) can be diluted with water or another fluid component, to provide a 5% component which can, as needed, be diluted up to about 5, ... about 20, ... about 50, ... about 75, or ... about 100 or more times, prior to or with use in conjunction with an active agent of the sort described herein, or in conjunction with one or more of the compositions described below. Alternatively rhamnolipid can be prepared using techniques and procedures known in the art, for instance as described in the aforementioned '232 and '090 patents.

Example 4

Nisin-containing compositions of this invention can be formulated as described in U.S. Pat. No. 5,763,395, the entirety of which is incorporated herein by reference. It will be understood by those skilled in the art made aware of this invention that representative compositions of this invention can be prepared using formulations of the sort described in the '395 patent but for the use of such a thioether stabilizer and inclusion of a rhamnolipid component of this invention. For instance, such compositions can be formulated as (a) an oral rinse, as described in the formulation of Example 1, therein; (b) a topical bacteriocide, as described in the formulation of Example 4, therein; and (c) a deodorant paste as described in the formulation of Example 6, therein. As would be understood by those skilled in the art, such compositions/formulations can be modified as described herein to include a rhamnolipid component, an amount of which for any end use application can be determined in a straight-forward manner without undue experimentation, and/or to reduce or minimize nisin content. Likewise, such compositions can be further modified to incorporate another active agent, in addition to or as a substitute for the nisin component.

Example 4d

| Ingredients | % |
|---|---|
| Water | 86.80 |
| Soymilk powder | 8.00 |
| Sugar | 4.00 |
| Flavor | 1.00 |
| Stabilizer | 0.10 |
| Nisin (1,000,000 IU/gram) | 0.03-0.05 |
| Rhamnolipid | 0.10 |

In accordance with various food material/product embodiments of this invention, the use of nisin combined with rhamnolipid in UHT soymilk can be used to extend the shelf-life and inhibit thermophilic spores. The amount/concentration of rhamnolipid can vary as described herein.

Example 5

Compositions of this invention comprising a natamycin component can be formulated as described in U.S. Pat. No. 6,844,004, the entirety of which is incorporated herein by reference. For instance, such compositions can be formulated as (a) topical creams, gels and ointments. (See, e.g., Examples 1-4, thereof.) As would be understood by those skilled in the art, such compositions/formulations can be modified as described herein to include a rhamnolipid component, an amount of which for any end use application can be determined in a straight-forward manner without any undue experimentation, and/or to reduce or minimize natamycin content. Likewise, such compositions can be further modified to incorporate another active agent of the sort described herein, in addition to or as a substitute for the natamycin component.

Example 6

Compositions of this invention can also comprise either nisin, natamycin or combinations thereof formulated directly into a processed food product as described in U.S. Pat. No. 6,146,675, the entirety of which is incorporated herein by reference. For instance, such compositions can be formulated as (a) a salad dressing as described in the formulation of Examples 1-2, therein; and (b) spreads as described in the formulations of Examples 3-4, therein. Again, as would be understood by those skilled in the art, such compositions/formulations can be modified as described herein to include a rhamnolipid component, the amount of which for any particular food product or end use application can be determined in a straight-forward manner without undue experimentation, and/or to reduce or minimize the nisin/natamycin content. Likewise, such compositions can be further modified to incorporate another active agent in addition to or as a substitute for the nisin/natamycin component.

Example 6c

| Ingredients | % |
|---|---|
| Water | 74.30 |
| Vinegar | 11.30 |
| Sodium Chloride | 2.0 |
| Sugar | 4.0 |
| Xanthan gum | 0.40 |
| Vegetable Oil | 5.30 |
| Natamycin | 20 ppm |
| Spices | 1.80 |
| Flavors | 0.90 |
| Rhamnolipid | 0.10 |

In accordance with various food product/material embodiments of this invention, the use of compositions comprising natamycin and rhamnolipid in salad dressing can be used to extend the shelf-life and inhibit mold growth. The amount/concentration of rhamnolipid can vary as described herein.

Example 6d

| Ingredients | % |
|---|---|
| Dry Cottage Cheese Curd | 74.26 |
| Cream (12% fat) | 25.00 |
| Sodium Chloride | 0.50 |
| Stabilizer | 0.10 |
| Natamycin | 20 ppm |
| Nisin (1,000,000 IU/gram) | 0.04 |
| Rhamnolipid | 0.01-0.10 |

In accordance with various food product/material embodiments of this invention, the use of compositions comprising natamycin, nisin, and rhamnolipid in cottage cheese can extend the shelf-life, inhibit mold growth, and inhibit bacterial growth, especially gram-positive and spore-forming bacteria.

Example 7

Various other compositions of this invention can be formulated for use in the delivery of plant micronutrients as described in U.S. Pat. No. 5,962,717, the entirety of which is incorporated herein by reference. For instance, such compositions can be formulated to provide (a) zinc, nickel, manganese, cobalt, molybdenum, boron and/or copper, as described in the corresponding examples, therein. As would be understood by those skilled in the art, such compositions/formulations can be modified as described herein to include a rhamnolipid component, an amount of which for any end use application can be determined in a straight-forward manner without undue experimentation, and/or to promote plant uptake and growth. Likewise, such compositions can be further modified to incorporate another active agent, in addition to or as a substitute for any particular micronutrient component.

Example 7b

| Ingredients | % |
| --- | --- |
| Ferrous Sulfate (FeSO$_4$) | 24.00 |
| Manganese Sulfate (MnSO$_4$) | 9.50 |
| Diammonium Sulfate (NH$_4$)$_2$SO$_4$ | 20.00 |
| Lignin Sulfonate | 15.00 |
| Humic Acid | 6.25 |
| Clay | 15.00 |
| Inert Filler | 9.25 |
| Rhamnolipid | 0.05-0.20 |

In accordance with various nutrient-containing embodiments of this invention, the addition of rhamnolipid in the above formulation can aid the uptake of the micronutrients by plants.

Example 8

Bakery compositions (e.g., cakes, donuts, breads, etc.) of this invention can be formulated as described in U.S. Pat. Nos. 4,416,903, 5,279,839, 5,049,389, and 6,635,289, each of which is incorporated herein by reference in its entirety. As would be understood by those skilled in the art, such bakery compositions/formulations can be modified as described herein to include a rhamnolipid component, an amount of which for any particular product or end-use application can be determined in a straight-forward manner without undue experimentation, to enhance texture and/or moisture retention and/or to reduce or minimize staling. Likewise, such compositions can be further modified to incorporate another active agent of the sort described herein.

Example 8a

| Evaluation of Rhamnolipid in Muffins | |
| --- | --- |
| INGREDIENTS | % |
| Unflavored Margarine | 9.7 |
| JENEIL Butter Flavor LB3500 | 0.4 |
| Sugar | 19.9 |
| Flour | 34.6 |
| Baking Powder | 1.9 |
| Milk | 24.3 |
| Whole Eggs | 9.7 |

| METHOD | |
| --- | --- |
| 1. | Soften margarine. |
| 2. | Mix eggs and milk. |
| 3. | Sift and dry blend sugar, flour, JENEIL LB3500 Butter Flavor and baking powder in a bowl. |

| Evaluation of Rhamnolipid in Muffins — continued | |
| --- | --- |
| 4. | Add egg and milk mixture alternating with butter until just mixed. |
| 5. | Put in muffin tins and bake for 12-15 minutes at 200° C. |

Muffins were prepared according to the formula above (control) and according to the formula above with 0.10% rhamnolipid added. The muffins prepared with rhamnolipid were moister, had an improved texture, and maintained freshness for a longer period of time. The amount/concentration of rhamnolipid can vary as described herein. In accordance herewith, with known recipe modifications, various other bakery products/compositions, including but not limited to cakes and donuts, can also be prepared.

Example 8b

| Evaluation of Rhamnolipid in Croissants | |
| --- | --- |
| INGREDIENTS | % |
| Pastry Vegetable Shortening -1 | 4.00 |
| JENEIL Butter Flavor LB3500 | 1.00 |
| Baker's Yeast | 0.85 |
| Hi Grade White Flour | 50.40 |
| Sugar | 0.85 |
| Salt | 0.831 |
| Skim Milk Powder | 2.87 |
| Water | 24.50 |
| Whole Eggs | 5.70 |
| Pastry Vegetable Shortening -2 | 9.00 |

| METHOD (Bread Maker) | |
| --- | --- |
| 1. | Add all ingredients except the second measure of butter/pastry fat), then set the machine to mix into dough (approx 45 minutes). |
| 2. | When the dough is completed, (add extra flour if needed) transfer into a bowl and cover. Refrigerate for 15 minutes. |
| 3. | While the dough cools, prepare the cold butter by placing it between two sheets of plastic or cling film. Using a rolling pin, roll the butter into a rectangular 10 × 15 cm and 5-7 mm thick and then remove the film. |
| 4. | From this stage, keep everything as cold as possible. Turn the dough onto a lightly floured board and roll into rectangle 25 × 35 cm. Lay the sheet of butter diagonally across this, and then fold the corners so the butter is completely contained in an envelope of dough. |
| 5. | Place on tray and refrigerate for 15 minutes. |
| 6. | Fold the chilled dough in half so the short ends meet, and roll gently into a rectangle 30 × 20 cm. Next fold the dough into thirds as you would fold a sheet of paper to put into an envelope. |
| 7. | Place on tray and refrigerate for 10 minutes. |
| 8. | Roll the dough again into a 30 × 20 cm rectangle, and then fold into thirds again. Roll out to 30 × 20 cm again and fold thirds once more before refrigerating for another 10 minutes. |
| 9. | Cut the dough in half lengthwise, and then roll the dough into rectangle 40 × 20 cm. With a sharp knife make diagonal cuts across the dough to make five or six fairly even triangles of dough. |
| 10. | Starting with the short side of the dough triangle towards you roll up loosely, moistening pointed end with little cold water to seal it down. Bend the pointed end inwards to form a crescent. |
| 11. | Repeat the same procedure until all the triangles are transformed. |
| 12. | Put in a greased baking tray and allow to rise in a warm draught-free place for 1-2 hours until double its original volume. |
| 13. | Brush with egg glaze (1 egg + 1 tbsp water + ½ tsp sugar) |
| 14. | Bake at 200° C. for 15-20 minutes until golden brown on top and underneath. |
| 15. | Cool on a rack. |

Croissants were prepared according to the formula above (control) and according to the formula above with 0.10% rhamnolipid added. The croissants prepared with rhamnolipid were moister, had an improved texture, maintained freshness for a longer period of time, and required a shorter proofing time than the control. The amount/concentration of rhamnolipid can vary as described herein.

Example 9

Various natamycin compositions can be formulated for use in the treatment of (a) food, animal feed and agricultural products, as described in U.S. Pat. Nos. 6,396,036 and 5,552,151, each of which is incorporated herein by reference in its entirety. As would be understood by those skilled in the art, such compositions/formulations can be modified as described herein to include a rhamnolipid component, an amount of which for any particular product or end-use application can be determined in a straight-forward manner without undue experimentation, and/or to reduce natamycin content. Likewise, such compositions can be further modified to incorporate another active agent, in addition to or as a substitute for any particular natamycin component.

Example 10

Beverage compositions of this invention can be formulated as described in U.S. Pat. No. 6,376,005, the entirety of which is incorporated herein by reference. As would be understood by those skilled in the art, such beverage compositions can be modified as described herein to include a rhamnolipid component, an amount of which for any particular product or end-use application can be determined in a straight-forward manner without undue experimentation, and/or to reduce natamycin content. Likewise, such compositions can be further modified to incorporate another active agent, in addition to or as a substitute for any particular natamycin component.

Example 11

Alternatively, compositions of this invention can be formulated for use as a dietary supplement, in the delivery of various human and animal nutrients, as described in the aforementioned, incorporated U.S. Pat. No. 6,503,545. For instance, such compositions can be formulated to provide (a) various vitamins, minerals and/or other micronutrients, as described in the corresponding examples, therein. As would be understood by those skilled in the art, such compositions/formulations can be modified as described herein to include a rhamnolipid component, an amount of which for any composition or end use application can be determined in a straight-forward manner without undue experimentation, and/or to promote a particular dietary condition. Likewise, such compositions can be further modified to incorporate another active agent, in addition to or as a substitute for any particular dietary nutrient component.

Example 12

Various other compositions of this invention can be formulated for use in the delivery of a naturally-occurring insecticide, as described in the aforementioned, incorporated U.S. Pat. No. 6,811,790. For instance, (a) neem-related compositions can be formulated as described in the formulation of Example 1, therein. Again, as would be understood by those skilled in the art, such compositions/formulations can be modified as described herein to include a rhamnolipid component, the amount of which for any particular insecticidal composition or end-use application can be determined in a straight-forward manner without undue experimentation, and/or to reduce or minimize the neem-related content. Likewise, such compositions can be further modified to incorporate another active agent in addition to or as a substitute for the neem-related component.

Example 12b

| Ingredients | % |
|---|---|
| Neem seed extract powder | 3.00 |
| 0.10-0.20% Rhamnolipid solution | 97.00 |

In accordance with various insecticide embodiments of this invention, the addition of a rhamnolipid component to insecticidal formulations may increase activity; e.g., of azadirachtin in neem seed extract. The amount/concentration of rhamnolipid can vary as described herein.

Example 13

Illustrating other embodiments, compositions of this invention can be formulated for use as or in the delivery of various synthetic insecticides as described in the aforementioned, incorporated U.S. Pat. No. 6,566,349. For instance, such compositions can be formulated with any one of a range of (a) organophosphorous compounds, including but not limited to those available under the diazinon and malathion trade designations. As would be understood by those skilled in the art, such compositions/formulations can be modified as described herein to include a rhamnolipid component, the amount of which for any particular insecticidal composition or end use application can be determined in a straight-forward manner without undue experimentation, and/or to reduce or minimize the content of the insecticidal component. Likewise, such compositions can be further modified to incorporate another active agent in addition to or as a substitute for the insecticidal component.

Example 14

Various other compositions of this invention can be formulated for use as or in the delivery of herbicides as described in the aforementioned, incorporated U.S. Pat. No. 6,184,182. For instance, such compositions can be formulated (a) in conjunction with N-phosphonomethylglycine as described in numerous examples, therein; (b) in conjunction with asulam as described in the formulations of Example 27, therein; (c) in conjunction with imazethapyr as described in the formulations of Example 30, therein; and (d) in conjunction with alachlor as described in the formulations of Example 32, therein. As would be understood by those skilled in the art, such compositions/formulations can be modified as described herein to include a rhamnolipid component, the amount of which for any particular herbicidal composition or end use application can be determined in a straight-forward manner without undue experimentation, and/or to reduce or minimize the herbicide content. Likewise, such compositions can be further modified to incorporate another active agent in addition to or as a substitute for the herbicidal component.

Example 15

Certain compositions of this invention can be formulated for use in the delivery of various chlorinated phenoxy herbicides as described in the aforementioned, incorporated U.S. Pat. No. 6,232,272. For instance, such compositions can be formulated to provide (a) herbicide compositions as described in the formulations of Examples 1 and 3-5, therein. Again, as would be understood by those skilled in the art, such compositions/formulations can be modified as described herein to include a rhamnolipid component, the amount of which for any particular herbicidal composition or end use application can be determined in a straight-forward manner without undue experimentation, and/or to reduce or minimize the content of the herbicidal component. Likewise, such compositions can be further modified to incorporate another active agent in addition to or as a substitute for the herbicidal component.

Example 16

Compositions of this invention can also comprise one or more plant hormone or growth regulator components as described in the aforementioned, incorporated U.S. Pat. Nos. 6,984,609 and 5,635,443. For instance, such compositions can be formulated to provide (a) gibberellin and/or indole 3-acetic acid components, as described in the formulations of the examples, therein. Alternatively, such compositions can also comprise a (b) humic acid component as described in the aforementioned, incorporated U.S. Pat. No. 5,698,001. Such compositions can be formulated as described in the corresponding examples. Again, as would be understood by those skilled in the art, such compositions/formulations can be modified as described herein to include a rhamnolipid component, the amount of which for any particular hormone/growth regulator composition or end use application can be determined in a straight-forward manner without undue experimentation, and/or to reduce or minimize the content of any one or more hormone/regulator components. Likewise, such compositions can be further modified to incorporate another active agent in addition to or as a substitute for the hormone/growth regulator component.

Example 16b

In accordance with this invention, one ton of animal feed can be sprayed with a composition comprising 200 ppm of rhamnolipid. The rhamnolipid tends to inhibit the growth of zoospores in the animal feed. The amount/concentration of rhamnolipid can vary as described herein.

Example 16c

| Ingredients | % |
|---|---|
| Gibberellin GA3 | 45.60 |
| Lactose Monohydrate | 52.70 |
| Lecithin | 1.20 |
| Rhamnolipid | 0.50 |
| TOTAL | 100.00 |

In accordance with various plant growth embodiments of this invention, the addition of rhamnolipid to a plant hormone/growth regulator formulation results in advantageous uptake for the plant, as well as allowing easier preparation and application of said formula. The amount/concentration of rhamnolipid can vary as described herein.

Example 17

More generally, alone or in conjunction with one or more of the preceding examples, compositions of this invention can comprise one or more active agents at least partially insoluble in water and as can be used in the form of a dispersion of such agent(s) in water or another medium, diluent or carrier component, such compositions as described in U.S. Pat. No. 6,413,908, the entirety of which is incorporated herein by reference. In particular, the active agent can be in the form of a (a) solution or dispersion in a non-aqueous water immiscible liquid, and used in conjunction with one or more surfactant or emulsifier components. As would be understood by those skilled in the art, such compositions can be modified as described herein to include a rhamnolipid component, the amount of which for any particular active agent or end use application can be determined in a straight-forward manner without undue experimentation, and/or to reduce or minimize the content of any one or more active agents. In particular, a rhamnolipid component of this invention can be used (b) in addition to or as a substitute for any one or more of the emulsifier/surfactant components otherwise used in the '908 patent.

We claim:

1. A composition comprising an active agent selected from plant growth regulators and combinations thereof; and a carrier component comprising a rhamnolipid, said composition on a substrate selected from plant components, plant shoots, plant seeds, plant produce, plant growth media and combinations thereof.

2. The composition of claim 1 wherein said rhamnolipid is selected from a monorhamnolipid, a dirhamnolipid and combinations thereof.

3. The composition of claim 1 wherein said carrier component comprises at least one of water, an alcohol, an oil, a fat, a wax, a gas and combinations thereof.

4. The composition of claim 1 wherein said plant growth regulators are selected from humic acid, indole 3-acetic acid and gibberellin.

5. A composition comprising a plant growth regulator selected from indole 3-acetic acid and gibberellin and combinations thereof; and a carrier component comprising a rhamnolipid.

6. The composition of claim 5 wherein said rhamnolipid is selected from a monorhamnolipid, a dirhamnolipid and combinations thereof.

7. The composition of claim 5 wherein said carrier component comprises at least one of water, an alcohol, an oil, a fat, a wax, a gas and combinations thereof.

8. The composition of claim 5 on a substrate selected from plant components, plant shoots, plant seeds, plant produce, plant growth media and combinations thereof.

* * * * *